United States Patent [19]
Lazarov et al.

[11] Patent Number: 6,110,204
[45] Date of Patent: Aug. 29, 2000

[54] IMPLANT

[75] Inventors: Miladin Lazarov; Isabella Mayer, both of Munich, Germany

[73] Assignee: Huber & Schussler, Munich, Germany

[21] Appl. No.: 08/913,268

[22] PCT Filed: Feb. 22, 1996

[86] PCT No.: PCT/DE96/00322

§ 371 Date: Feb. 9, 1998

§ 102(e) Date: Feb. 9, 1998

[87] PCT Pub. No.: WO96/25960

PCT Pub. Date: Aug. 29, 1996

[30] Foreign Application Priority Data

Feb. 22, 1995 [DE] Germany .......................... 195 06 188

[51] Int. Cl.$^7$ .............................. A61F 2/00; A61L 27/04; A61L 27/28; A61L 33/00
[52] U.S. Cl. ..................... 623/11.11; 623/1.46; 623/23.6; 427/2.24; 427/453; 427/126.3; 606/76; 428/304.4; 428/315.5
[58] Field of Search ................................. 623/11, 16, 18, 623/12; 606/76; 604/265; 427/2.24, 453, 126.3; 428/304.4, 315.5

[56] References Cited

U.S. PATENT DOCUMENTS

| 3,643,658 | 2/1972 | Steinemenan . |
| 4,098,956 | 7/1978 | Blickensderfer et al. . |
| 5,152,794 | 10/1992 | Davidson .................................. 606/76 |
| 5,670,248 | 9/1997 | Lazarov et al. . |
| 5,776,556 | 7/1998 | Lazarov et al. . |

FOREIGN PATENT DOCUMENTS

| 0 295 397 A1 | 12/1988 | European Pat. Off. . |
| 0 410 711 A1 | 1/1991 | European Pat. Off. . |
| WO 95/17533 | 6/1995 | WIPO . |

OTHER PUBLICATIONS

Dion, et al., "Haemocompatibility of Ti6A14V Alloy," *Biomaterials*—14(2):122–126 (1993).

Bolz, et al., "Haemocompatibility Optimisation of Implants by Hybrid Structuring," *Med. & Biol. Eng. & Comput.*,—31:S123–S130 (1993).

Brady, Robert F., Jr., "Coming to an Unsticky End," *Nature*—368(3):16–17 (1994).

Kondo, et al., "Manufacture of Prosthetic Implants from Titanium and Its Alloy," Abstract (1992).

Kondo, et al., "Ceramic–coated Prosthetic Implants," Abstract (1989).

*Primary Examiner*—Mickey Yu
*Assistant Examiner*—Choon P. Koh
*Attorney, Agent, or Firm*—Albert P. Halluin; J. David Smith; Howrey Simon Arnold & White, LLP

[57] ABSTRACT

The present invention relates to an implant for use in the human body, an implant substrate being coated with a material which contains chemical compounds between one or more metals (M) of group IV A of the periodic system, nitrogen (N) and oxygen (O), 2 to 45% of the volume in the coating material being formed by voids whose sizes range from $(0.4 \text{ nm})^3$ to $(50 \text{ nm})^3$, and the remaining volume having a composition of a metal of group IV A of the periodic system to nitrogen to oxygen of 1:(0.1 to 1.7):(0.1 to 1.7), a material having formula $MN_xO_y$ (wherein x,y= 0.1–1.7) resulting.

The invention also relates to the use of this implant for implantation into the animal or human body.

16 Claims, 2 Drawing Sheets a b c

IMPLANT

The present application is a U.S. nationalization pursuant to 35 U.S.C. 371 of PCT/DE96/00322 filed on Feb. 22, 1996 which is in turn based on German Patent Application No. 195 06 188.8 filed on Feb. 22, 1995.

This invention relates to implants.

Various artificial materials are introduced into the human body as a short-term or relatively long-term implant for diagnosis and treatment (catheters, probes, sensors, stents, artificial heart valves, endotracheal tubes etc.). The selection of the material for these implants depends on the stability and geometry required to insure a certain function of the implant. In order to meet these functional demands, it is often not possible to pay sufficient regard to the fact of whether these materials are biocompatible. Therefore, it is useful to improve the materials from which these implants are made by coatings which are compatible with blood and tissue. Coatings are required which activate the coagulation system only to a minor degree, and which cause few endogenous defense reactions thus reducing the deposit of thrombi and biofilm on the implant surface. A coating is useful for all materials which are directly introduced into the bloodstream, e.g. for vascular prostheses, stents, artificial heart valves, as well as for implants which are in contact with tissue, e.g. cardiac pacemakers or defibrillators and for implants which are in contact with body fluids, e.g. bile duct drains, catheters for draining urea and cerebrospinal fluid, and endotracheal resuscitation tubes. The blood compatibility of implants is influenced decisively by their surface properties. In order to avoid the formation of thrombi ("antithrombogeneity"), relative smoothness is necessary to prevent the deposit and destruction, of corpuscular components of the blood and activation of the coagulation system. In addition, direct charge exchange processes must be prevented between coagulation-specific proteins and the implant surface.

It is known to use coatings made of pyrolytic carbon as a common material for heart valves to meet these demands. In addition, it is known to use semi-conducting materials, e.g. a-SiC:H as an implant coating, to prevent the charge exchange processes between the coagulation-specific proteins and the implant surface (A. Bolz, M. Schaldach, "Haemocompatibility optimisation of implants by hybrid structuring", Med. & Biol. & Comput., 1993, 31, pp. 123–130). Furthermore, it is known to employ $Ti_6Al_4V$ as a coating (I. Dion, C. Baquey, J.- R. Monties, P. Havlik, "Haemocompatibility of $Ti_6Al_4V$ alloy", Biomaterials, Vol. 4, 1993, pp. 122–126). A plurality of plastics have also been investigated in the field of polymer chemistry to produce non-adhering surfaces. In this field as well, the problem has not yet been solved satisfactorily (R. F. Brady Jr., "Coming to an unsticky end", Nature, Vol. 368, 1994, pp. 16–17).

Although implants having a carbon coating and a porous structure meet the demands made on the surface properties, they have the drawback that an electron transfer caused by tunneling of occupied, valence band-like states of the protein to free states of the solid leads to cleavage of fibrinogen in the blood. The resulting fibrin monomers polymerize and produce an irreversible thrombus. Although implants made of rutile ceramics prevent these charge exchange processes, they were not ready for series production because of the high production costs. Although implants having a coating made of amorphous carbon (a-SiC:H) can be produced in a cost-effective fashion, the drawback of this material consists in that it is not hard enough for certain applications. This material is presently produced by means of CVD methods which require great heating of the substrate as an additional problem, so that application is made more difficult for a large number of heat-sensitive basic materials. In addition, this material has a fixed band gap and low conductivity. Both properties lead to the formation of thrombi rather than preventing them.

Therefore, it is the object of the present invention to provide an implant of the above-mentioned kind with a surface by which the activation of blood coagulation accompanied by the formation of thrombi as well as the formation of a biofilm are reduced significantly.

The object is achieved by an implant according to the present invention.

An implant within the meaning of this invention shall comprise every device or every means which can be implanted into an animal or human body or inserted therein on a relatively long-term basis and short-term basis, respectively, or be attached to the animal or human body. The following examples are mentioned: catheters, probes, sensors, stents, artificial heart valves, endotracheal tubes, cardiac pacemakers.

The material for coating the implant, i.e. the coating material, contains the following chemical compounds: one or more metals of the IVA group of the periodic table, nitrogen and oxygen. 2–45%, preferably 10–43%, more preferably 20–35%, of the volume is formed by voids whose sizes range from $(0.4\ nm)^3$ $[=0.064\ nm^3]$ to $(50\ nm)^3$ $[\approx 125000\ nm^3]$, preferably $(0.4\ nm)^3$ to $(20\ nm)^3$. The gaps frequently described in the literature (e.g. John A. Thornton, The microstructure of sputter-deposited coatings, J. Vac. Sci. Technol. A4 (6), 1986, pp. 3059–3065) and formed by columnar film growth are not meant to be within the scope of these voids. Thus, it is not the known gaps between the columns that are of concern but rather voids within these columns. These very voids result in the properties specific to the invention. The remaining volume of the coating material (98–55%, preferably 90–57%, especially preferably 80–65%) has a composition of a metal of group IVA of the periodic table to nitrogen to oxygen such as 1:(0.1 to 1.7):(0.1 to 1.7), preferably 1:(0.4 to 1.2):(0.1 to 1.2). The formula of the material is $MN_xO_y$, "M" being a metal of group IVA of the periodic table and x and y, respectively, being values from 0.1 to 1.7. The above ratios refer to the particle number and molar ratios, respectively. The metal of group IVA of the periodic table may be titanium, zirconium or hafnium or a mixture of two or the three metals. Preferably, it is titanium.

As far as the sizes of the voids are concerned, it is preferred that they occur in the lower range, i.e. that they are preferably not greater than $(15\ nm)^3$. The "remaining volume" of the material preferably comprises one or more chemical compounds selected from the group consisting of $MN_x$ (x=0.7 to 1.2), $MO_x$ (x=0.7 to 1.2), Magnelli phases of the M—O system ($MnO_{2n-1}$), $MO_2$, $M_2N$ (wherein M=metal of group IVA of the periodic system) as well as about 0–30%, preferably 0.5–5%, of carbon compounds of a metal of group IVA of the periodic table. By the addition of these carbon compounds the spectrum of possible uses of the coating is extended and the stability is increased, which has been shown e.g. in the case of urine catheters. Minor amounts of titanium carbides as impurities are usually not disturbing, they even permit a cheaper production of the coating. The possibility that the chemical phases may preferably be present in the coating material in crystalline or amorphous form, prevents the apposition and destruction of corpuscular components of the blood, so that the involved activation of the coagulation system is prevented. Therefore, the coating material counteracts the formation of thrombi, i.e. shows "antithrombogenic" properties.

The possibility of introducing a fractual size distribution of the voids, permits an essential extension of the surface as used e.g. for pacemaker electrodes. A greater surface permits a reduction of the electrical impedance and thus a longer service life of a pacemaker battery.

Furthermore, the coating material preferably includes that the real part of the refractive index for the X-ray wavelength of 0.0709 nm ranges from 0.9999984 to 0.9999973. The mass density of the coating material preferably ranges from 3.5 to 5.4 g/cm$^3$, preferably from 3.7 to 4.5 g/cm$^3$, more preferably from 3.8 to 4.2 g/cm$^3$.

In addition to the metals of group IVA of the periodic table, the coating material may also contain niobium, tantalum, tungsten, molybdenum or alloys thereof as additional metals, which improves the corrosion resistance of the coating.

When the material contains hydrogen (dissolved or preferably in bound form), free bonds are saturated in the amorphous phases. This affects the electron state distribution which is more favorable for biocompatibility.

The thickness of the coating ranges preferably from 3 nm to 3 mm, more preferably from 10 nm to 2 mm, most preferably from 30 to 71 nm.

The coating preferably has a specific resistance ranging from 30 to 30000 $\mu\Omega$.cm, preferably 100 to 6000 $\mu\Omega$.cm, more preferably 2000 to 3000 $\mu\Omega$.cm. The specific resistance can be adjusted without any problem by the selection of the void fraction or portion. The specific resistance of the material increases when voids are added. For example, the specific resistance of TiN$_{0.98}$O$_{0.2}$ may be 70 $\mu\Omega$.cm when the void portion is 3% and increases up to about 650 $\mu\Omega$.cm when the void portion is 40%.

The coating is disposed as a thin layer on a substrate suitable as an implant. This substrate may be made of plastics, e.g. polyester, polyamide, polyurethane (PUR), polyethylene (PE), polytetrafluoroethylene (PTFE) or DACRON$^R$ or of a metal such as molybdenum, silver, gold, copper, aluminum, tungsten, nickel, chromium, zirconium, titanium, hafnium, tantalum, niobium, vanadium, iron or the mixtures or alloys thereof. The coating formed as a thin layer is applied preferably onto a rough substrate surface whose roughness is characterized by a random distribution of the deviations from the mean level and the standard deviation of this distribution ranges from 0 to 1500 nm, preferably 40 to 120 nm.

The coating may additionally be coated with at least one further thin layer selected from the group consisting of one or more oxides, preferably SiO$_2$, TiO$_2$, ZrO$_2$, HfO$_2$, Al$_2$O$_3$, Y$_2$O$_2$, niobium, molybdenum, tungsten and tantalum oxides.

In a preferred embodiment, an intermediate layer producing adhesive strength is provided between the substrate and the coating. This intermediate layer comprises a metal, preferably chromium, copper, nickel, molybdenum, tantalum, niobium, silver or alloys of these met als, or a semiconductor.

Growth of endogenous cells, which serves particularly for anchoring the implant but also for inducing the formation of a physiological surface, can be controlled by the composition of the material surface. The surface coating can be applied to many different basic materials (substrates), e.g. metals and plastics, having differing geometry. A special advantage of the implants according to the invention is represented by the cost-effective production as w ell as the fact that as a function of the chosen method the coating can also be applied to materials which d o not tolerate heating because of their special structure.

The coating can be made by means of both the CVD method and the PVD method, but especially preferably by the PVD method. In particular, the following process is suited for the production of the implants according to the invention: While the metal of group IVA of the periodic table is deposited onto a substrate suitable as an implant, an oxide, nitride or carbide compound forms by maintaining a gas atmosphere which contains at least one of the gases N$_2$, O$_2$, CH$_4$ and/or noble gases. In this connection, the condensation of the metal particles on a heatable or coolable substrate is controlled via the total gas pressure p$_{tot}$, the deposition rate r, the substrate temperature T$_{sub}$ and by the distance 1 existing between metal source and substrate, such that the volume fraction of voids is 2 to 45% by volume, whose sizes range from (0.4 nm)$^3$ to (50 nm)$^3$. The production parameters are chosen as follows:

T$_{sub}$=−5 to 400° C., l=0.01 to 1.5 m the partial pressure ratio of the introduced gases N$_2$ and O$_2$:
(P$_{N2}$/P$_{O2}$)=1 to 2000, P$_{tot}$=2×10$^{-5}$ hPa–4×10$^{-2}$ hPa and r=0.01 to 60 nanometers/s.

For the production process it is necessary to adjust the production parameters such that the portion of voids is foreseeable. This can be done by the following procedure: the following applies to substrate temperatures ranging from preferably 100 to 220° C. and a distance of the vapor source to the substrate 1 ranging preferably from 0.5 to 1.2 m:

A volume fraction of 34% of voids will be achieved if $$K = P_{tot} \cdot r/1 = (1 \text{ to } 3) \cdot 10^{-4} \frac{\text{mBar nm}}{\text{sm}}$$

and the total gas pressure P$_{tot}$ ranges from 0.7×10$^{-3}$ hPa to 2×10$^{-2}$ hPa.

A volume fraction of 20% of voids is achieved when a choice is made within the range of $$K = P_{tot} \cdot r/1 = (0.2 \text{ to } 0.5) \cdot 10^{-4} \frac{\text{mBar nm}}{\text{sm}}.$$

Volume fractions between 20 and 34% may be adjusted by chosing the magnitude K according to the following equation:

$$K = ((0.04 \text{ to } 0.2) \cdot \text{desired void portion} - 0.7) \cdot 10^{-4} \frac{\text{mBar nm}}{\text{sm}}$$

Thus, there is the possibility of producing the desired void portion in the material according to the invention by adjusting rate r, the total gas pressure P$_{tot}$ and the distance l.

By analogy, the volume fraction of the voids in the layer can be controlled for the substrate temperatures ranging from preferably 250 to 400° C. and l ranging from preferably 0.5 to 1.2 m as follows: A volume fraction of e.g. 40% of voids will be achieved if $$K = (6 \text{ to } 8) \cdot 10^{-4} \frac{\text{mBar nm}}{\text{sm}}$$

and P$_{tot}$ ranges from 2×10$^{-2}$ hPa to 4×10$^{-2}$ hPa. If K is chosen within the range of $$K = (0.8 \text{ to } 1.9) \cdot 10^{-4} \frac{\text{mBar nm}}{\text{sm}},$$

the volume fraction of the voids will be 20%. In order to realize values between 20 and 40% of volume fractions, K has to be chosen according to the equation:

$$K = ((0.12 \text{ to } 0.31) \cdot \text{desired void portion} - 0.4) \cdot 10^{-4} \frac{\text{mBar nm}}{\text{sm}}.$$

Volume fractions therebetween can be determined by linear interpolation in each case. Small volume fractions of voids (2–20%) are achieved with small rates of 0.01–0.1 nm/s and at low gas pressures of $10^{-4}$–$2 \times 10^{-4}$ mBar. Very large void portions (>40%) are achieved at high total gas pressures of >$4 \times 10^{-2}$ mbar: At these gas pressures, the material may be present as a loose compound. The coating is effected on a substrate which is suited as an implant as defined above.

In the case of plastic implants $T_{sub}$ must, of course, be chosen such that plastics do not change, i.e. $T_{sub}$ should be preferably 5 to 20 Kelvin below the transformation temperature of the plastics.

The coating is deposited on the substrate in a usual vacuum deposition apparatus as is common to a person skilled in this field.

As compared to the formerly used materials, the advantage of the coating material of the present invention consists particularly in that it is possible to vary between differing states (metallic, dielectric). As a result, the composition of the material can be adjusted such that it may have attracting or repelling properties for body cells, blood protein components or microorganisms.

The material has a portion of voids whose volume fraction may be increased or lowered as desired. By the void portion, the band structure can be adapted to the demands without changing the chemical composition. Thus, the positive properties of the coating material are lost very rapidly when the void size is above $(50 \text{ nm})^3$. In addition, the growth or adhering of living cells can be increased or decreased by the well-calculated selection of the void portion. In this connection, it is preferred that in addition to the above-described voids ranging from $(0.4 \text{ nm})^3$ to $(50 \text{ nm})^3$ the coating also contains greater voids above $(500 \text{ nm})^3$. This supports the growth of the implant in given cell structures or also the growth of cells onto the coated surface. This is supported by the fact that the implant material to be coated (i.e. the substrate) may have a rough surface. The surface roughness is preferably between 0–1500 $\mu$m.

Another advantage is that the material can be supplied with depot substances, preferably coagulation-inhibiting substances or antibiotics, which are then continuously released from the material.

The surface coating of the implant according to the invention is especially advantageous because the described material has a conductivity which prevents the formation of volume charges activating fibrinogen. In addition, the described coating material has an electron density which does not permit a space current from fibrinogen to the implant. This property also prevents the activation of fibrinogen. These positive properties of the described material are adjusted in two ways: on the one hand, by varying the voids within the claimed range and, on the other hand, by varying the chemical composition. Both possibilities serve for achieving that the electron density of the coating is on the energetic level of the protein states in the blood. In addition, it is beneficial that the coating be developed in such a way that the charge exchange processes occurring between the coagulation-specific proteins and the implant surface are prevented.

The implant can be used for implantation or short-term or long-term introduction into or attachment to the animal or human body.

The invention is now described in more detail with reference to the figures.

Figure 3:
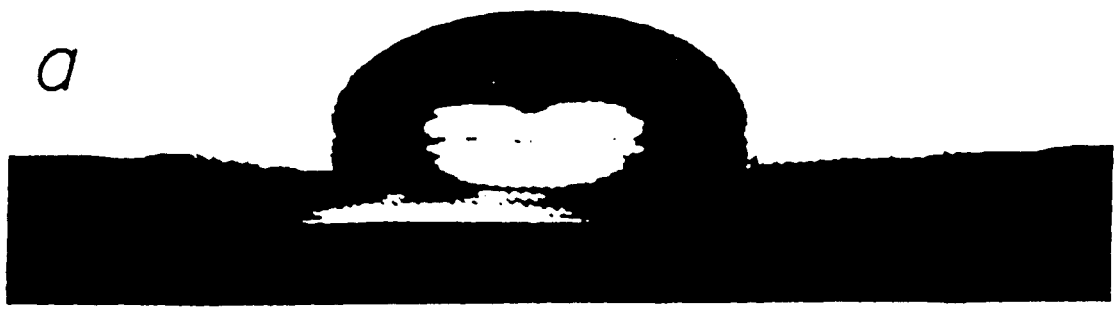
Figure 3:
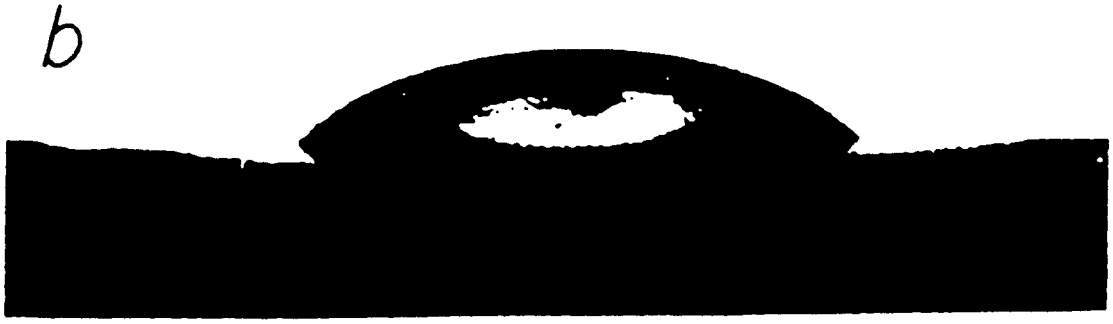
Figure 3:

FIG. 3 shows contact angle pictures of 3 modifications of $TiN_xO_y$ (wherein x=1.0 and y=1.1, but the void portions vary) relative to water. In (a), the void portion is 40%, in (b), it is 22%, and in (c), it is 3%. The adhesive properties are controlled by the void portion.

The invention is now described in more detail with reference to the examples:

EXAMPLES

Example 1

The surface of a heart valve prosthesis made of the basic material titanium was coated with a coating of $TiN_xO_y$ (x=1.2 and y=0.6; measured by means of Elastic Recoil Detection (ERD)). The coating was produced by means of reactive evaporation with selection of the following parameters: substrate temperature=250° C., distance between evaporator and substrate=45 cm; partial pressure ratio ($N_2$ to $O_2$)=1500; total pressure=$7 \times 10^{-4}$ hPa; deposition rate=0.2 nm/s.

The void portion in the coating material was around 28% and the void size was between $(0.6 \text{ nm})^3$ and $(0.9 \text{ nm})^3$.

Figure 1:
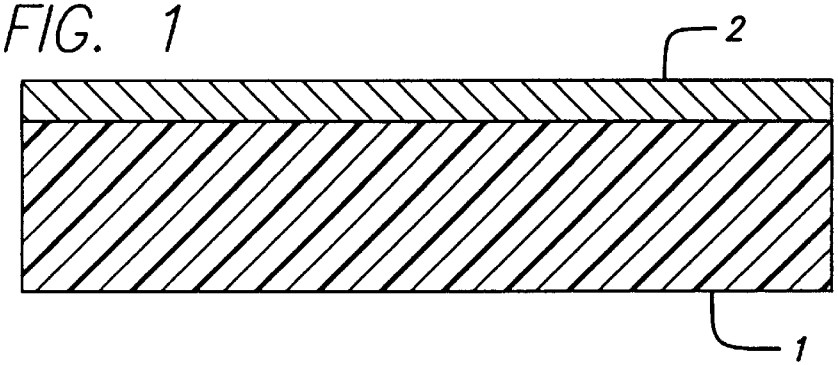
FIG. 1 shows a section through the coating of an implant

FIG. 1 shows a section through the coated heart valve prosthesis, (1) representing the surface of the basic material and (2) denoting the coating. The coating (2) has a thickness of 3 $\mu$m.

Example 2

Six endotracheal tubes were coated. The coating was produced by means of reactive evaporation with selection of the following parameters: substrate temperature=250° C., distance between evaporator (metal source) and substrate 45 cm; total pressure=$7 \times 10^{-4}$ hPa; deposition rate=0.2 nm/s. The partial pressure ratio ($N_2$ to $O_2$) of the supplied gas es was varied.

The void portion in the coating material was around 24%, and the void size was between $(0.6 \text{ nm})^3$ and $(0.9 \text{ nm})^3$.

Figure 2:
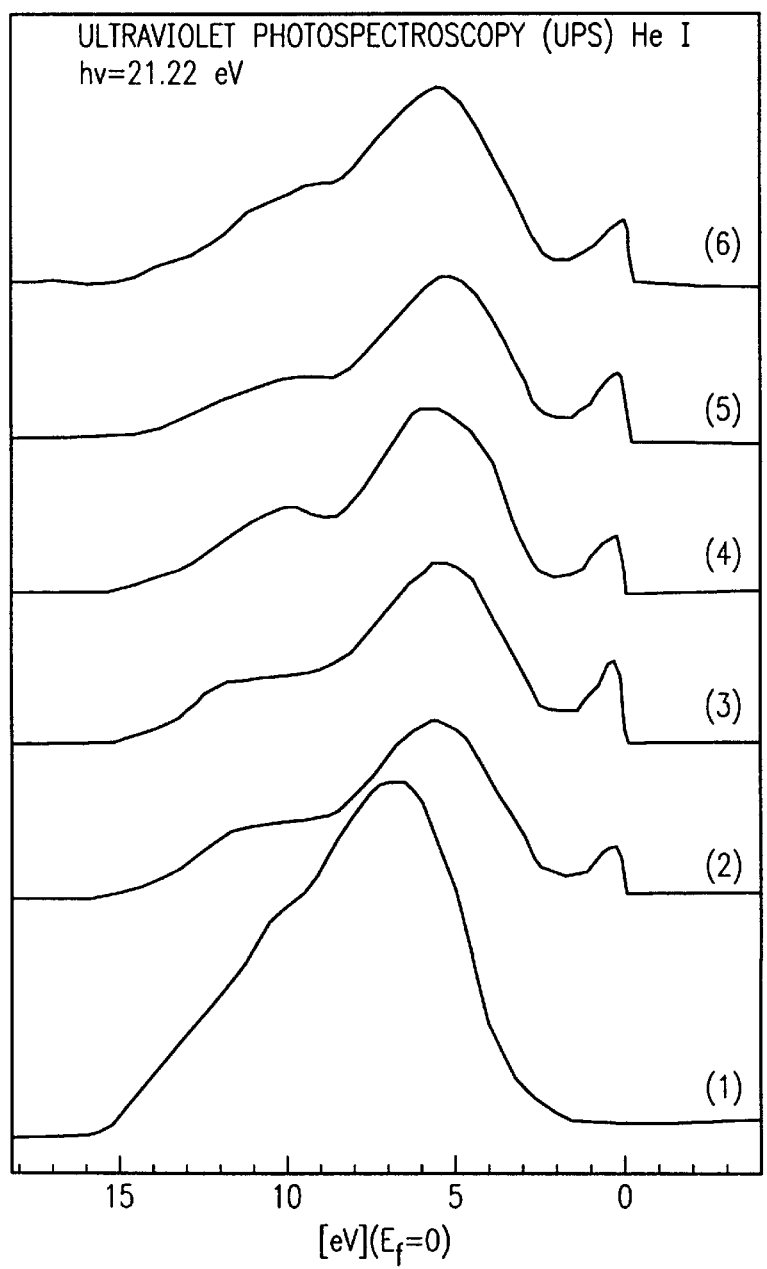
FIG. 2 shows UPS spectra of six coatings of endotracheal tubes

UPS spectra which are shown in FIG. 2 were made of the six coatings.

Graph (1): Coating of $TiN_xO_y$ wherein x=0.5 and y=1.4, measured by means of Elastic Recoil Detection (ERD). The partial pressure ratio ($N_2$ to $O_2$) was 120.

Graph (2): Coating of $TiN_xO_y$ wherein x=0.9 and y=1.2, measured by means of Elastic Recoil Detection (ERD). The partial pressure ratio ($N_2$ to $O_2$) was 500.

Graph (3): Coating of $TiN_xO_y$ wherein x=0.9 and y=0.8, measured by means of Elastic Recoil Detection (ERD). The partial pressure ratio ($N_2$ to $O_2$) was 900.

Graph (4): Coating of $TiN_xO_y$ wherein x=0.9 and y=0.2, measured by means of Elastic Recoil Detection (ERD) The partial pressure ratio ($N_2$ to $O_2$) was 1200.

Graph (5): Coating of $TiN_xO_y$ wherein x=1.4 and y=0.3, measured by means of Elastic Recoil Detection (ERD) The partial pressure ratio ($N_2$ to $O_2$) was 1600.

Graph (6): Coating of $TiN_xO_y$ wherein x=1.5 and y=0.15, measured by means of Elastic Recoil Detection (ERD) The partial pressure ratio ($N_2$ to $O_2$) was 2000.

The coatings on which graphs (2) to (6) are based markedly show a Fermi level which is correlated with conductivity.

Example 3

Three differing coating materials of $TiN_xO_y$ (x=1.0, y=1.1) were applied by means of vacuum deposition onto endotracheal tubes and contact angle pictures of the three coatings were made. The results are shown in FIG. 3. (a) is the picture of a sample having a 40% void portion, (b) is that of a sample having a 22% void portion, and (c) is that of a sample having a 3% void portion.

The parameters chosen for the production of the coating were:

in the sample having 40% of void portion :
  distance between metal source and substrate=70 cm
  substrate temperature $T_{sub}$=300° C.
  partial pressure ratio ($P_{N2}/P_{O2}$)=1200
  deposition rate r=0.01 nm/s
  total gas pressure=$2 \times 10^{-2}$ hPa
  A void size between $(0.8 \text{ nm})^3$ and $(2.8 \text{ nm})^3$ resulted.

in the sample having a void portion of 22%:
  distance between metal source and substrate=70 cm
  substrate temperature $T_{sub}$=300° C.
  partial pressure ratio ($P_{N2}/P_{O2}$)=1200
  deposition rate r=0.25 nm/s
  total gas pressure=$2 \times 10^{-4}$ hPa
  A void size between $(0.6 \text{ nm})^3$ and $(0.9 \text{ nm})^3$ resulted.

in the sample having a void portion of 3%:
  distance between metal source and substrate=70 cm
  substrate temperature $T_{sub}$=300° C.
  partial pressure ratio ($P_{N2}/P_{O2}$)=1200
  deposition rate r=0.7 nm/s
  total gas press=$2 \times 10^{-4}$ hPa
  A void size between $(0.4 \text{ nm})^3$ and $(0.8 \text{ nm})^3$ resulted.

As follows from FIG. 3, the adhesive properties of the coating can be controlled by varying the void portion.

What is claimed is:

1. An implant, comprising a substrate coated with a thin layer of a coating material, wherein said coating material comprises one or more metals (M) of group IV A of the periodic table, nitrogen (N) and oxygen (O), and wherein 2 to 45% of the volume in the coating material is formed by voids whose sizes range from $(0.4 \text{ nm})^3$ to $(50 \text{ nm})^3$ and the remaining volume comprises a composition of a metal of group IV A of the periodic table, nitrogen and oxygen in a ratio of 1:(0.1 to 1.7):(0.1 to 1.7), such that a material having the formula $MN_xO_y$ wherein x,y=0.1–1.7 results.

2. The implant according to claim 1, wherein the coating material further comprises one or more of the following chemical compounds:
  $MN_x$ wherein x=0.7 to 1.2
  $MO_x$ wherein x=0.7 to 1.2
  Magnelli phases of the M—O system ($M_nO_{2n-1}$)
  $MO_2$
  $M_2N$
wherein M is a metal of group IV A of the periodic table.

3. The implant according to any one of claims 1 to 2, wherein the coating material contains small amounts of carbon compounds of a metal of group IV A of the periodic table.

4. The implant according to any one of claim 1 or 2, wherein the metals (M) of group IV A of the periodic table, nitrogen (N) and oxygen (O) may occur in the coating material in crystalline or amorphous form.

5. The implant according to any one of claim 1 or 2, wherein the real part of the refractive index of the coating material for the X-ray wavelength of 0.0709 nm ranges from 0.9999984 to 0.9999973.

6. The implant according to any one of claim 1 or 2, wherein the mass density of the coating material ranges from 3.5 to 5.4 g/cm$^3$.

7. The implant according to any one of claim 1 or 2, further comprising at least one compound selected from the group consisting of niobium, tantalum, tungsten, molybdenum and alloys thereof.

8. The implant according to any of claim 1 or 2, wherein the coating material further comprises hydrogen.

9. The implant according to any one of claim 1 or 2, wherein the layer thickness of the coating material on the substrate ranges from 3 nm to 3 mm.

10. The implant according to any one of claim 1 or 2, wherein the specific resistance ranges from 30 to 300000 $\mu\Omega$cm.

11. The implant according to any of claim 1 or 1, wherein the coating material is applied as a thin layer onto a rough substrate surface wherein the roughness is characterized by a random distribution of deviations from a mean level wherein a standard deviation of the distribution ranges from 0 to 1500 $\mu$m.

12. The implant according to any one of claim 1 or 2, wherein the thin coating layer is coated with at least one further thin layer comprising one or more oxides selected from the group consisting of $SiO_2$, $TiO_2$, $ZrO_2$, $HfO_2$, $Al_2O_3$ $Y_2O_3$, niobium oxide molybdenum oxide, tungsten oxide and tantalum oxide.

13. The implant according to any one of claim 1 or 2, wherein at least one further thin layer, made of a metal or a semi-conductor is introduced between the substrate and the coating.

14. The implant according to any one of claim 1 or 2, wherein the coating material is applied onto a metallic substrate comprising molybdenum, silver, gold, copper, aluminum, tungsten, nickel, chromium, zirconium, titanium, hafnium, tantalum, niobium, vanadium, iron and one or more alloys thereof.

15. The implant according to any one of claim 1 or 2, wherein the coating material is applied onto a plastics substrate comprising a polyester, a polyamide, a polyurethane (PUR), a polyethylene (PE), a polytetrafluoroethylene (PTFE) or DACRON$^R$.

16. The implant according to any one of claim 1 or 2, wherein the voids range from $(0.4 \text{ nm})^3$ to $(50 \text{ nm})^3$ and the coating material has voids greater than $(500 \text{ nm})^3$.

* * * * *